(12) United States Patent
Huie, Jr. et al.

(10) Patent No.: US 7,058,455 B2
(45) Date of Patent: *Jun. 6, 2006

(54) INTERFACE FOR MAKING SPATIALLY RESOLVED ELECTRICAL CONTACT TO NEURAL CELLS IN A BIOLOGICAL NEURAL NETWORK

(75) Inventors: Philip Huie, Jr., Cupertino, CA (US); Daniel V. Palanker, Sunnyvale, CA (US); Harvey A. Fishman, Menlo Park, CA (US); Alexander Vankov, Mountain View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 112 days.

This patent is subject to a terminal disclaimer.

(21) Appl. No.: 10/742,584

(22) Filed: Dec. 19, 2003

(65) Prior Publication Data

US 2004/0230270 A1 Nov. 18, 2004

Related U.S. Application Data

(60) Provisional application No. 60/447,796, filed on Feb. 14, 2003, provisional application No. 60/447,421, filed on Feb. 14, 2003.

(51) Int. Cl.
*A61N 1/05* (2006.01)
(52) U.S. Cl. .......................... 607/116; 607/53
(58) Field of Classification Search ................ 607/53, 607/54, 116; 623/6.63
See application file for complete search history.

(56) References Cited

U.S. PATENT DOCUMENTS

| | | | |
|---|---|---|---|
| 3,955,560 A | 5/1976 | Stein et al. ............. 128/2.1 |
| 4,628,933 A | 12/1986 | Michelson ............. 128/419 |
| 5,109,844 A | 5/1992 | de Juan, Jr. et al. ......... 128/419 |
| 5,575,813 A * | 11/1996 | Edell et al. ............. 607/116 |
| 6,032,062 A | 2/2000 | Nisch ................. 600/372 |
| 6,324,429 B1 | 11/2001 | Shire et al. ............ 607/54 |
| 6,347,250 B1 | 2/2002 | Nisch et al. ............ 607/54 |
| 6,393,327 B1 | 5/2002 | Scribner ............... 607/54 |
| 2002/0169486 A1 | 11/2002 | Chow et al. ............ 607/54 |
| 2003/0032946 A1 | 2/2003 | Fishman et al. ......... 604/890.1 |

(Continued)

OTHER PUBLICATIONS

Stephen A. Boppart et al., "A Flexible Perforated Microelectrode Array for Extended Neural Recordings," IEEE Transactions on Biomedical Engineering, vol. 39, No. 1, Jan. 1992.

(Continued)

*Primary Examiner*—George Manuel
*Assistant Examiner*—Lenwood Faulcon, Jr.
(74) *Attorney, Agent, or Firm*—Lumen Intellectual Property Services, Inc.

(57) ABSTRACT

An interface for selective excitation or sensing of neural cells in a biological neural network is provided. The interface includes a membrane with a number of channels passing through the membrane. Each channel has at least one electrode within it. Neural cells in the biological neural network grow or migrate into the channels, thereby coming into close proximity to the electrodes.

Once one or more neural cells have grown or migrated into a channel, a voltage applied to the electrode within the channel selectively excites the neural cell (or cells) in that channel. The excitation of these neural cell(s) will then transmit throughout the neural network (i.e. cells and axons) that is associated with the neural cell(s) stimulated in the channel.

31 Claims, 9 Drawing Sheets

U.S. PATENT DOCUMENTS

2005/0203601 A1* 9/2005 Palanker et al. ............ 607/116

OTHER PUBLICATIONS

Lars Wallman et al., "Perforated Silicon Nerve Chips with Doped Registration Electrodes: in Vitro Performance and in Vivo Operation," IEEE Transactions on Biomedical Engineering, vol. 46, No. 9, Sep. 1999.

Kovacs et al., "Regeneration Microelectrode Array for Peripheral Nerve Recording and Stimulation," IEEE Transactions on Biomedical Engineering, vol. 39, No. 9, pp. 893-902 Sep. 1992.

Wallman et al., "Perforated Silicon Nerve Chips with Doped Registration Electrodes: in Vitro Performance and in Vivo Operation," IEEE Transactions on Biomedical Engineering, vol. 46 No. 9 pp. 1065-1073 Sep. 1999.

Boppart et al., "A Flexible Perforated Microelectrode Array for Extended Neural Recordings," IEEE Transactions on Biomedical Engineering, vol. 39, No. 1, pp. 37-42, Jan. 1992.

Huie et al., "Perforated Membrane as an Interface for Focal Electrical Stimulation of Retina," Investigative Ophthalmology & Visual Science 2003; 44: E-Abstract 5055.

Huie et al., "Tissue-engineered Neurite Conduits to Connect Retinal Ganglion Cells to an Electronic Retinal Prosthesis," Investigative Ophthalmology & Visual Science 2002; 43: E-Abstract 4475.

* cited by examiner

INTERFACE FOR MAKING SPATIALLY RESOLVED ELECTRICAL CONTACT TO NEURAL CELLS IN A BIOLOGICAL NEURAL NETWORK

CROSS REFERENCE TO RELATED APPLICATIONS

This application claims priority from U.S. provisional applications 60/447,796 and 60/447,421, both filed on Feb. 14, 2003, and both hereby incorporated by reference.

GOVERNMENT SPONSORSHIP

This invention was made with US Government support under contract FA8750-04-C-0043 from the Air Force Research Lab. The Government has certain rights in this invention.

FIELD OF THE INVENTION

The present invention relates generally to electrical stimulation or sensing of neural cells. More particularly, the present invention relates to an electrode configuration for selectively making electrical contact to neural cells.

BACKGROUND

Several degenerative retinal diseases that commonly lead to blindness, such as retinitis pigmentosa and age-related macular degeneration, are primarily caused by degradation of photoreceptors (i.e., rods and cones) within the retina, while other parts of the retina, such as bipolar cells and ganglion cells, remain largely functional.

Accordingly, an approach for treating blindness caused by such conditions that has been under investigation for some time is provision of a retinal prosthesis connected to functional parts of the retina and providing photoreceptor functionality.

Connection of a retinal prosthesis to functional parts of the retinal is typically accomplished with an array of electrodes (see, e.g., U.S. Pat. No. 4,628,933 to Michelson). Michelson teaches a regular array of bare electrodes in a "bed of nails" configuration, and also teaches a regular array of coaxial electrodes to reduce crosstalk between electrodes. Although the electrodes of Michelson can be positioned in close proximity to retinal cells to be stimulated, the electrode configurations of Michelson are not minimally invasive, and damage to functional parts of the retina may be difficult to avoid.

Alternatively, a prosthesis having electrodes can be positioned epiretinally (i.e., between the retina and the vitreous humor) without penetrating the retinal internal limiting membrane (see, e.g., U.S. Pat. No. 5,109,844 to de Juan et al.). Although the arrangement of de Juan et al. is less invasive than the approach of Michelson, the separation between the electrodes of de Juan et al. and retinal cells to be stimulated is larger than in the approach of Michelson.

Such increased separation between electrodes and cells is undesirable, since electrode crosstalk and power required to stimulate cells both increase as the separation between electrodes and cells increases. Furthermore, increased electrical power has further undesirable effects such as increased resistive heating in biological tissue and increased electrochemical activity at the electrodes.

U.S. Pat. No. 3,955,560 to Stein et al. is an example of an approach which provides low separation between electrodes and nerve fibers (i.e., axons), but requires a highly invasive procedure where a nerve is cut and then axons regenerate through a prosthesis and past electrodes embedded within the prosthesis.

OBJECTS AND ADVANTAGES

Accordingly, an objective of the present invention is to provide apparatus and method for selectively making electrical contact to neural cells with electrodes in close proximity to the cells and in a minimally invasive manner.

Another objective of the present invention is to instigate or allow migration of the neural cells towards the stimulating electrodes in order to minimize the distance between an electrode and a cell.

Yet another objective of the present invention is to preserve functionality of a biological neural network when instigating or allowing migration of neural cells.

Still another objective of the present invention is to reduce cross-talk between neighboring electrodes.

Another objective of the present invention is to ensure low threshold voltage and current for cell excitation.

Yet another objective of the present invention is to provide an interface that allows for mechanical anchoring of neural tissue to a prosthesis.

Still another objective of the present invention is to provide a large electrode surface area to decrease current density and thereby decrease the rate of electrochemical erosion.

An advantage of the present invention is that a selected cell or group of neural cells can be brought into proximity to stimulating or sensing electrodes while preserving the signal processing functionality of a biological neural network. A further advantage of the present invention is that by bringing cells into close proximity to electrodes, electrical power required for cell excitation is reduced, thus decreasing tissue heating and electrode erosion. Another advantage of the present invention is that close proximity between cells and electrodes reduces cross-talk with non-selected cells, thus allowing a higher packing density of electrodes which provides improved spatial resolution.

SUMMARY

The present invention provides an interface for selective excitation or sensing of neural cells in a biological neural network. The interface includes a membrane with a number of channels passing through the membrane. Each channel has at least one electrode within it. Neural cells in the biological neural network grow or migrate into the channels, thereby coming into close proximity to the electrodes.

Once one or more neural cells have grown or migrated into a channel, a voltage applied to the electrode within the channel selectively excites the neural cell (or cells) in that channel. The excitation of these neural cell(s) will then transmit throughout the neural network (i.e., cells and axons) that is associated with the neural cell(s) stimulated in the channel. Alternatively, excitation of a neural cell (or cells) within the channel due to activity within the biological neural network is selectively sensed by the electrode within the channel.

DETAILED DESCRIPTION OF THE DRAWINGS

Figure 1:
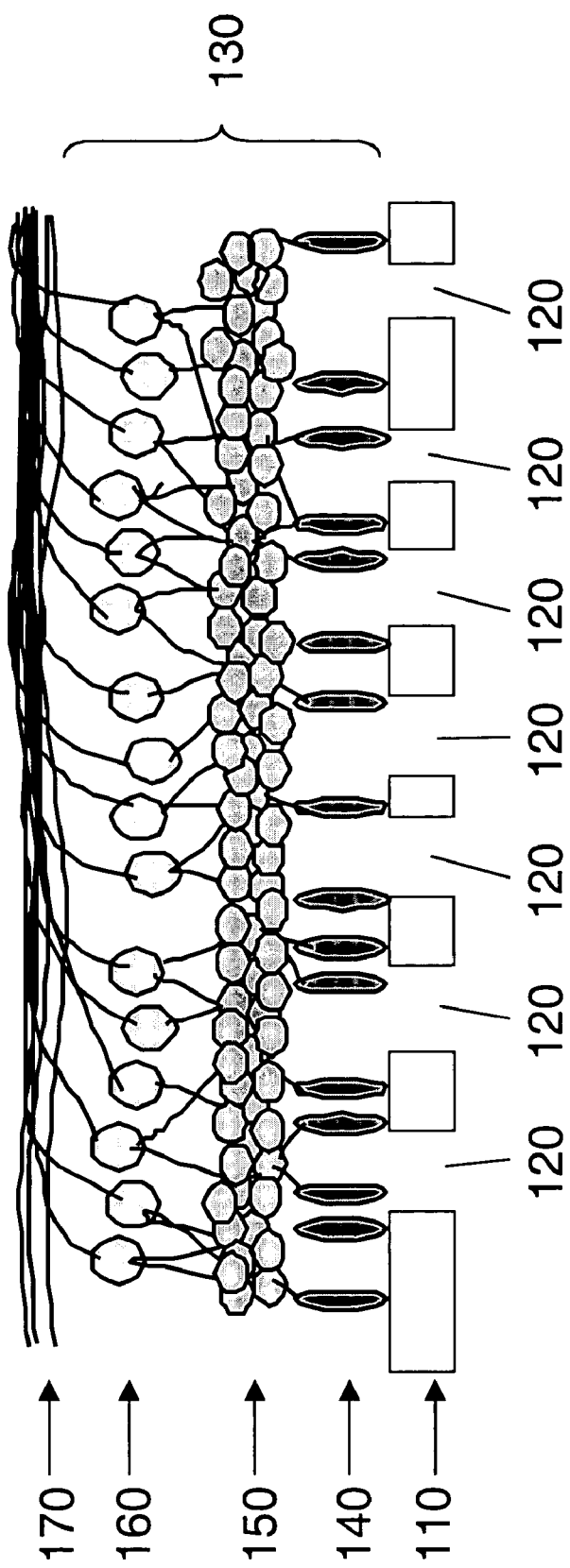
FIG. 1 shows an embodiment of the invention having a membrane with channels positioned under a retina.

FIG. 1 shows an embodiment of the invention having a membrane 110 with a plurality of channels 120 passing through membrane 110. In the example of FIG. 1, membrane 110 is preferably positioned under a retina 130. Exemplary retina 130 includes photoreceptors (i.e., rods and/or cones) 140, inner nuclear layer cells 150 (e.g., bipolar cells), ganglion cells 160 and respective axons connecting to an optic nerve 170. Membrane 110 can be of any type of biocompatible material that is substantially electrically non-conductive and is flexible enough to conform to the shape of the neural tissue in a biological neural network. Suitable materials for membrane 110 include mylar and PDMS (polydimethylsiloxane). The thickness of membrane 110 is less than 0.5 mm, and is preferably between about 5 microns and about 100 microns. Channels 120 pass completely through membrane 110 and can be of any shape, although substantially circular shapes are preferred. Retina 130 on FIG. 1 is an example of a biological neural network. The invention is applicable to making electrical contact to any kind of biological neural network, including but not limited to: central nervous system (CNS) neural networks (e.g., brain cortex), nuclei within the CNS, and nerve ganglia outside the CNS. A biological neural network is made up of interconnected biological processing elements (i.e., neurons) which respond in parallel to a set of input signals given to each.

Figure 2:
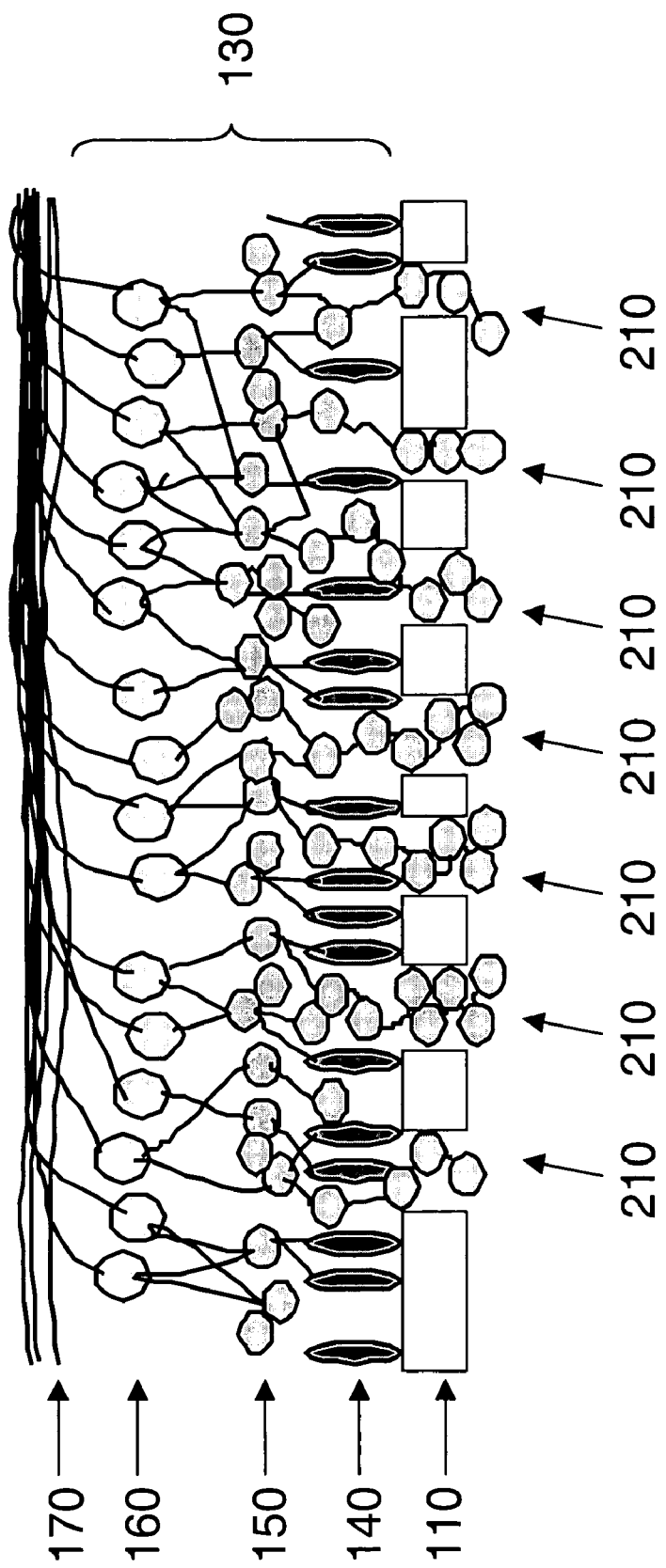
FIG. 2 shows an embodiment of the invention having a membrane with channels positioned under a retina, and having cells from the inner nuclear layer migrated into the channels.

FIG. 2 shows cell migration into channels 120 of membrane 110 of FIG. 1. When membrane 110 is positioned near a layer of neural tissue, neural cells in the neural tissue layer will tend to grow or migrate towards the channels. This growth process is a natural physiological response of cells and may depend on the existence of nutrients, space and a suitable surface morphology for these cells. Optionally, a growth (or inhibition) factor could be included to enhance (or decrease) the migration or growth of the neural cells. Such factors include but are not limited to: BDNF (brain-derived neurotrophic factor, CNTF (ciliary neurotrophic factor), Forskolin, Laminin, N-CAM and modified N-CAMs. However, such a growth or inhibition factor is not always necessary. In the example of FIG. 2, cells 210 are neural cells 150 which have migrated into and/or through channels 120 in membrane 110 positioned subretinally. The diameter of each channel should be sufficient to allow migration of neural cells 150, and is preferably in a range from about 5 microns to about 20 microns. We have found experimentally that such cell migration tends to occur easily when membrane 110 is disposed subretinally (i.e. between the retina and the outer layers of the eye), and tends not to occur easily (or at all) when membrane 110 is disposed epiretinally (i.e. between the retina and the vitreous humor). Penetration of neural cells 150 into and through channels 120 provides mechanical anchoring of retina 130 to membrane 110.

Figure 4:
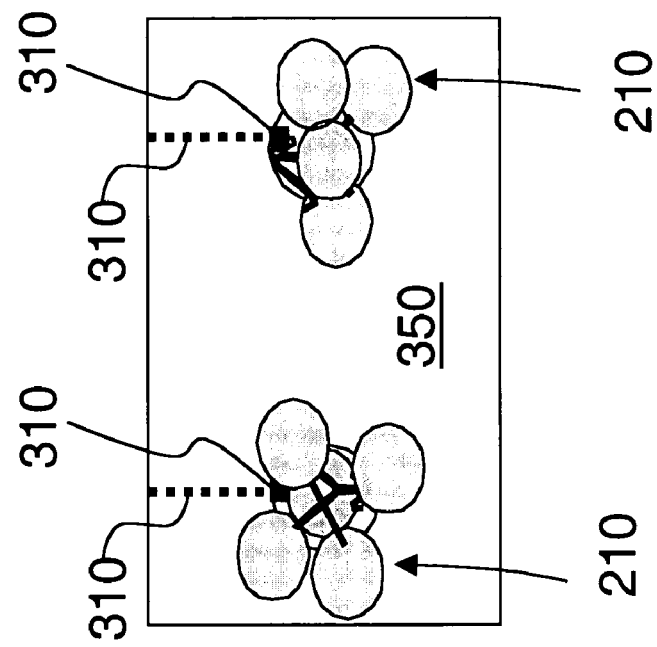
FIG. 4 shows a bottom view of an embodiment of the invention according to FIG. 3.
Figure 3:
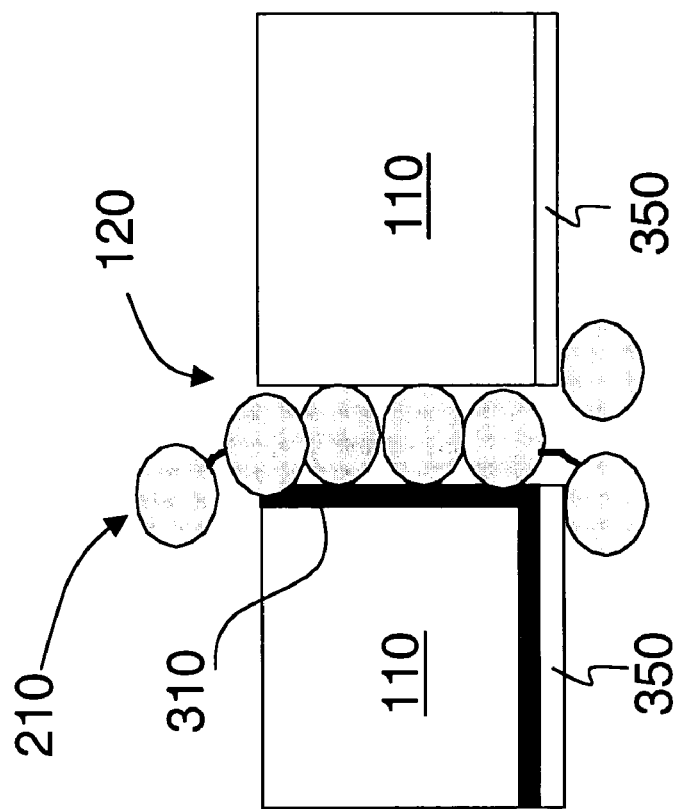
FIG. 3 shows a side view of an embodiment of the invention having a membrane with an electrode exposed inside the channel and coated outside the channel at the bottom of the membrane.

FIG. 3 shows an enlarged view of one of the channels of the configuration of FIG. 2. In the example of FIG. 3, an electrode 310 is positioned inside channel 120 in membrane 110 leaving enough space for neural cells 210 and their axons to migrate and grow through the channel. As a result of this cell migration, electrode 310 is in close proximity to neural cells 210. Electrode 310 is shown extending to a bottom surface of membrane 110 (i.e., a surface of membrane 110 facing away from the biological neural network). Wires (not shown) can connect electrodes 310 to input and/or output terminals (not shown), or to circuitry within membrane 110. In such cases where electrodes 310 and optionally wires are present on the bottom surface of membrane 110, a non-conductive layer 350 is preferably disposed on the bottom surface of membrane 110 covering electrodes 310 (and any wires, if present) to provide electrical isolation. FIG. 4 shows a view as seen looking up at non-conductive layer 350 of two channels 120 having the configuration of FIG. 3. FIG. 4 also shows close proximity between electrodes 310 and cells 210.

Electrodes 310 are in electrical contact with neural cells 210, but may or may not be in physical contact with neural cells 210. Direct physical contact between electrodes 310 and cells 210 is not necessary for electrodes 310 to stimulate cells 210, or for electrodes 310 to sense activity of cells 210.

Figure 5:
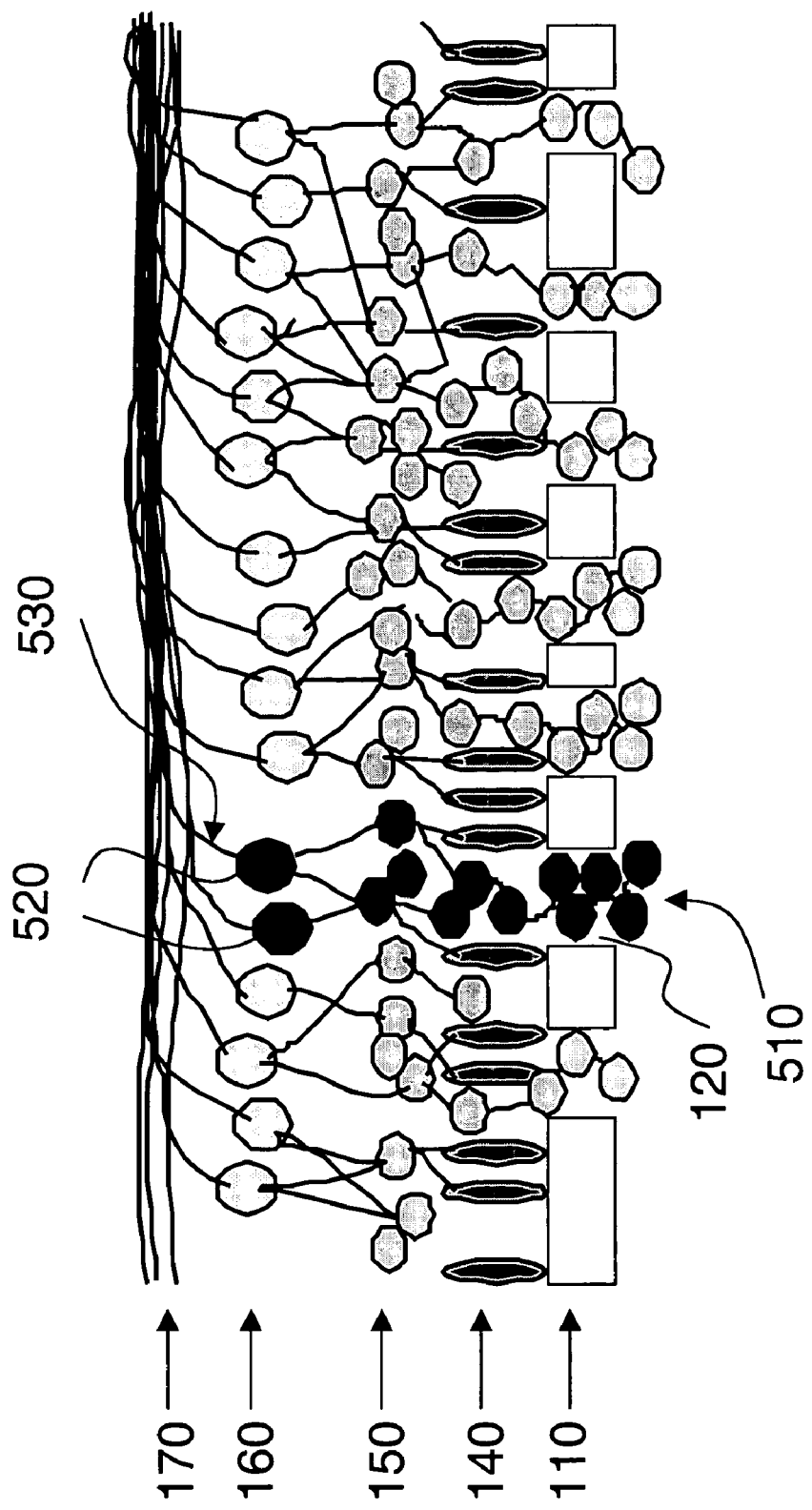
FIG. 5 shows an embodiment of the invention having a membrane with channels positioned under a retina, and having neural cells migrated into the channels. Voltage applied to a channel electrode causes excitation of neural cells in that channel. The excited neural cells in that channel transmit signal(s) to the retinal network.

FIG. 5 shows operation of the configuration of FIG. 2. A selected neural cell (or cells) 510 within one of channels 120 is electrically excited by an electrode within the same channel. Impulses from neural cell (or cells) 510 excite selected ganglion cells 520, which in turn excite selected optic nerve fibers 530.

Many advantages of the present invention are provided by the configurations discussed in connection with FIGS. 1–5. In particular, close proximity between electrodes 310 and migrated cells 210 is provided, which reduces the electrical power required to stimulate cells 210 and decreases cross-talk to unselected cells (i.e., cells not within the channel 120 corresponding to a particular electrode 310). Reduction of electrical power required to stimulate cells 210 leads to reduced tissue heating and to reduced electrochemical erosion of electrodes 310. Reduction of cross-talk to unselected cells provides improved spatial resolution. Furthermore, electrodes 310 are well insulated from each other by membrane 110, so electrode to electrode cross-talk is also reduced. Additionally, the growth and/or migration of neural cells 150 into channels 120 preserves existing functionality of retina 130.

However, the configurations shown in FIGS. 1–5 do not directly limit growth and/or migration of cells through channels 120. In some cases, we have found that many cells grow or migrate through channels 120, leading to the formation of significant uncontrolled "tufts" of cells and/or cell processes facing away from the retina. Such uncontrolled tuft growth can lead to fusing of adjacent tufts, which tends to undesirably increase crosstalk. Also, electrodes 310 have a small surface area, which increases current density and thus increases undesirable electrochemical activity at electrodes 310.

Figure 6:
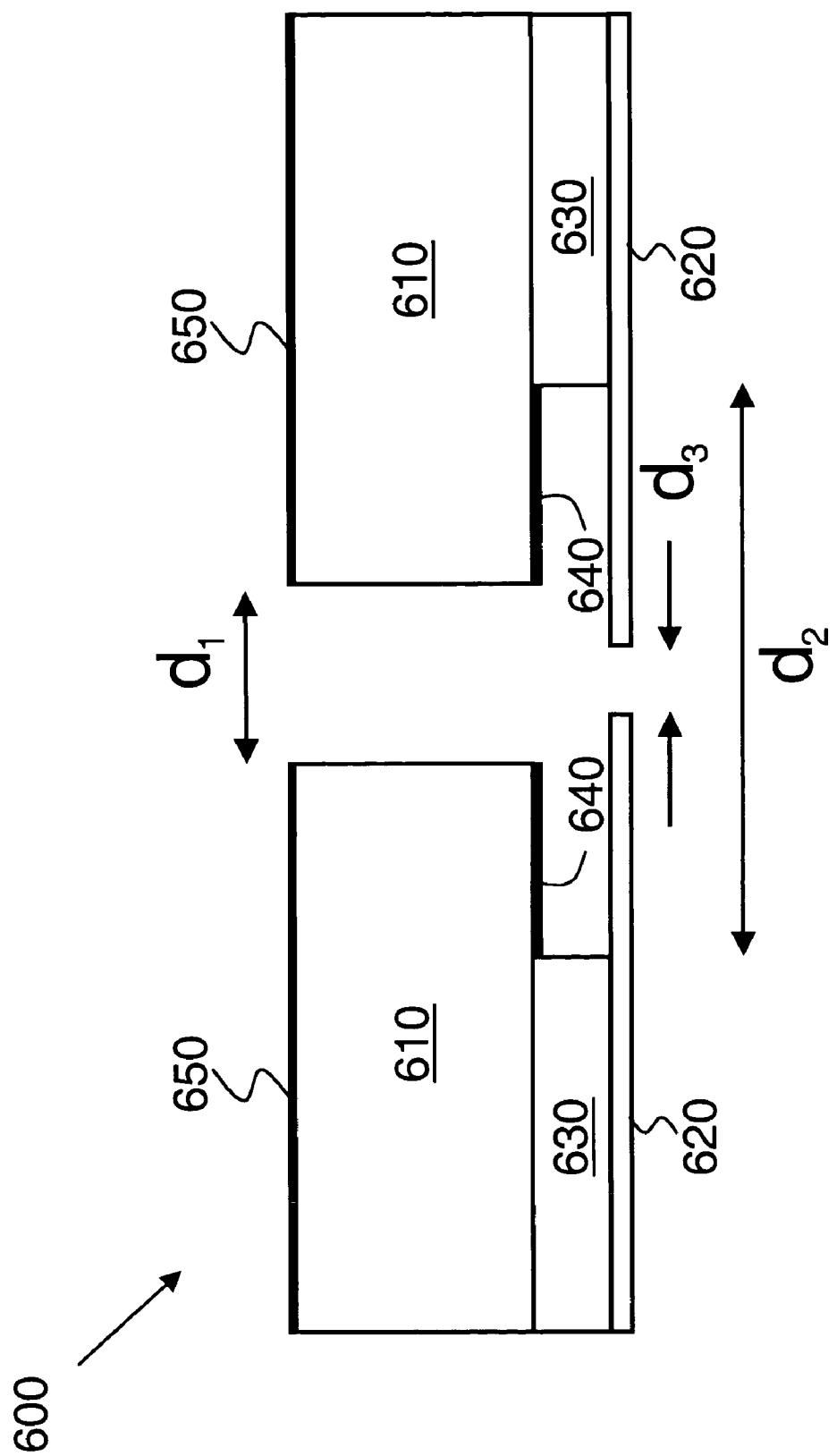
FIG. 6 shows an embodiment of the invention having channels with two different channel diameters, and having a stop layer at the bottom to prevent cell migration past the channel while allowing nutrient flow.

FIG. 6 shows an interface 600 according to an embodiment of the invention which prevents the formation of such uncontrolled retinal tufts and provides increased electrode surface area. In the embodiment of FIG. 6, a first layer 610 and a second layer 630 form a membrane analogous to membrane 110 of FIG. 1. A channel passes through both first layer 610 and second layer 630, where the channel diameter d2 in second layer 630 is larger than the channel diameter d1 in first layer 610. The thickness of layers 610 and 630 together is less than 0.5 mm. The thickness of layer 610 is preferably between about 10 microns and about 50 microns. The thickness of layer 630 is preferably between about 5 microns and about 50 microns. A stop layer 620 is disposed such that second layer 630 is in between first layer 610 and stop layer 620. Stop layer 620 is shown as having a hole with diameter d3 aligned to the channel through layers 610 and 630. An electrode 640 is disposed on a surface of first layer 610 facing second layer 630.

Layers 610, 620, and 630 can be of any type of biocompatible material that is substantially electrically non-conductive and is flexible enough to conform to the shape of the neural tissue in a biological neural network. Suitable materials include mylar and PDMS (polydimethylsiloxane).

First layer 610 is in proximity to and faces a biological neural network (not shown on FIG. 6). Retina 130 as shown on FIG. 1 is an example of such a biological neural network. As discussed above in connection with FIG. 2, cells tend to grow or migrate into channels within layer 610, provided there is sufficient room. Accordingly, the diameter d1 should be sufficiently large to allow migration of neural cells (such as 150 on FIG. 1), and is preferably in a range from about 5 microns to about 50 microns.

The function of stop layer 620 is to prevent uncontrolled growth of a retinal tuft past stop layer 620, while permitting nutrients to flow to a cell (or cells) within the channel passing through layers 610 and 630. Therefore, diameter d3 should be small enough to prevent growth or migration of cells (or cell process) through stop layer 620. Preferably, d3 is less than about 5 microns in order to prevent cell migration through stop layer 620. Alternatively, stop layer 620 can include several small holes each having a diameter of less than about 5 microns, where the holes in layer 620 are aligned with the channel within second layer 630. More generally, stop layer 620 can be either an impermeable membrane having at least one hole in it large enough to permit nutrient flow and small enough to prevent cells from moving through it, or a membrane which is permeable to nutrient flow.

Since diameter d2 is larger than diameter d1, a retinal tuft may form within the channel through second layer 630. Such retinal tuft formation is not uncontrolled, since the maximum size of the retinal tuft is determined by stop layer 620. In fact, controlled retinal tuft formation is likely to be desirable, since it will tend to provide improved mechanical anchoring of interface 600 to a retina.

Electrode 640 is disposed on a surface of first layer 610 facing second layer 630 and within the channel passing through the two layers. Since d2 is greater than d1, the surface area of electrode 640 can be made significantly larger than the area of an electrode within a channel having a uniform channel diameter along its length (such as shown on FIG. 3). The diameter d2 is preferably from about 10 microns to about 100 microns. In the example of FIG. 6, an electrode 650 is disposed on the top surface of first layer 610. An applied voltage between electrodes 640 and 650 provides an electric field within the channel passing through first layer 610.

One variation of the present invention is to coat electrode 640 to further increase its surface area and to further decrease the current density and associated rate of electrochemical erosion of the conductive layer. For example, carbon black has a surface area of about 1000 $m^2/g$ and so a coating of carbon black on electrode 640 can significantly increase its effective surface area. Other suitable materials for such a coating include platinum black, iridium oxide, and silver chloride.

Laser processing can be used to form channels. In the case of the embodiment of FIG. 6, the largest holes (i.e. the channels through second layer 630) are formed first, then layers 630 and 610 are attached to each other. The next largest holes are then formed, using the previously formed holes for alignment, and stop layer 620 is then attached to second layer 630. Finally, the smallest holes (if necessary) are formed in stop layer 620, using previously formed holes for alignment. Electrodes 640 on first layer 610 can also be formed by laser processing. For example, first layer 610 can have a continuous film of metal deposited on the surface of layer 610 that will eventually face toward second layer 630, and laser processing of this continuous film of metal can define electrodes 640 (and optionally wires connected to these electrodes as discussed in connection with FIG. 3). Laser processing methods to perform these tasks are known in the art.

Figure 7:
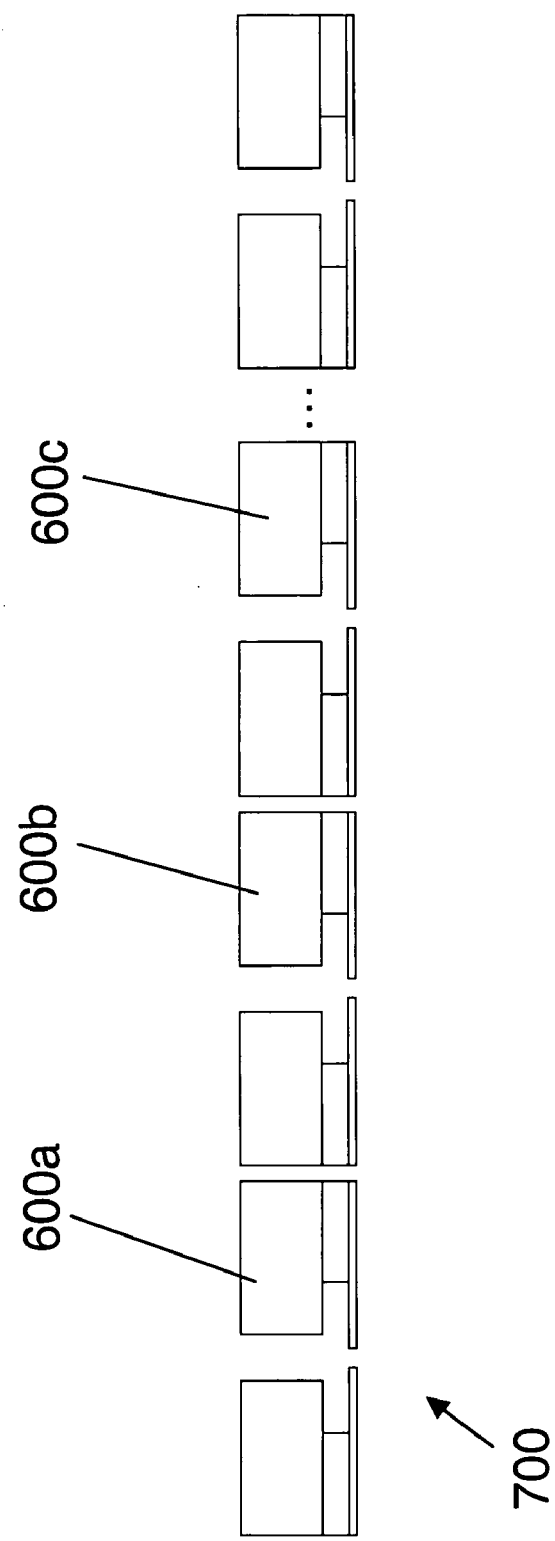
FIG. 7 shows an embodiment of an array according to the present invention.

FIG. 7 shows an interface 700 including several interfaces 600 (shown as 600a, 600b, 600c, etc.) according to FIG. 6, for making selective contact to multiple points in a retina. Typically, interfaces 600 within interface 700 are arranged as a two-dimensional array, where each channel corresponds to a pixel of the array. In the embodiment of FIG. 7, electrode 650 is preferably a common electrode for all channels. Resistance between electrodes 640 corresponding to different array elements is largely determined by the diameter d3 of the hole in stop layer 620, since conduction is mainly through extra cellular fluid surrounding interfaces 600. Accordingly, the selection of d3 (or equivalently, the total open area in stop layer 620) is determined by a tradeoff between reducing electrode to electrode cross-talk (by decreasing d3) and providing sufficient nutrient flow (by increasing d3).

Figure 8:
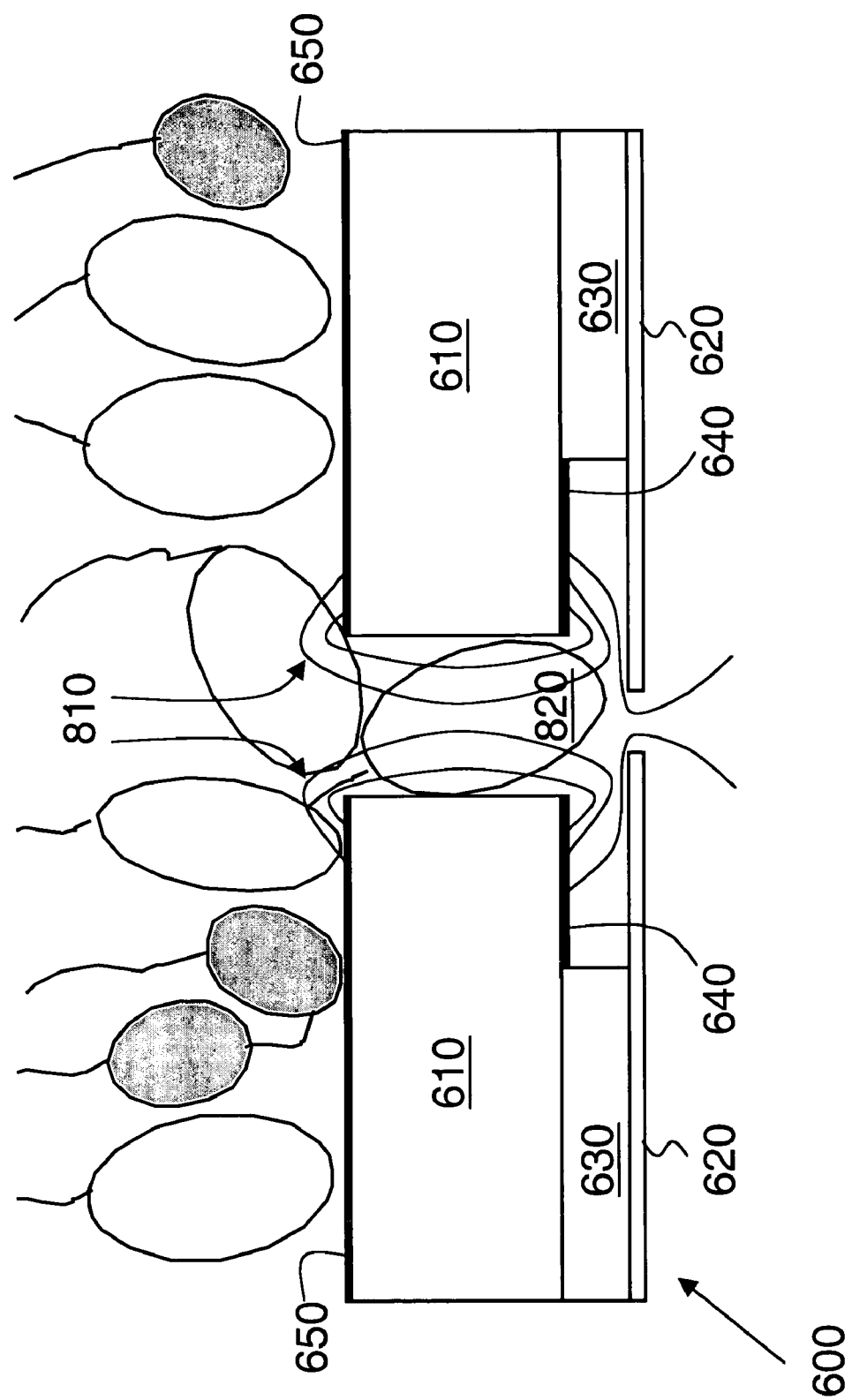
FIG. 8 shows an embodiment of the invention where only a few (ideally one) neural cells can enter the channel. An electric field is applied across the cell providing efficient stimulation.

FIG. 8 shows operation of interface 600, where a single cell 820 has migrated into the channel passing through first layer 610. In practice, several cells may be present in this channel, although the ideal situation of having only a single cell in the channel is preferred because it provides maximum selectivity of excitation. A potential difference between electrodes 640 and 650 creates an electric field 810 passing through cell 820 as shown. Electric field 810 depolarizes cell 820 to stimulate it, and the resulting signal travels into the rest of the retina as indicated in FIG. 5.

Figure 9:
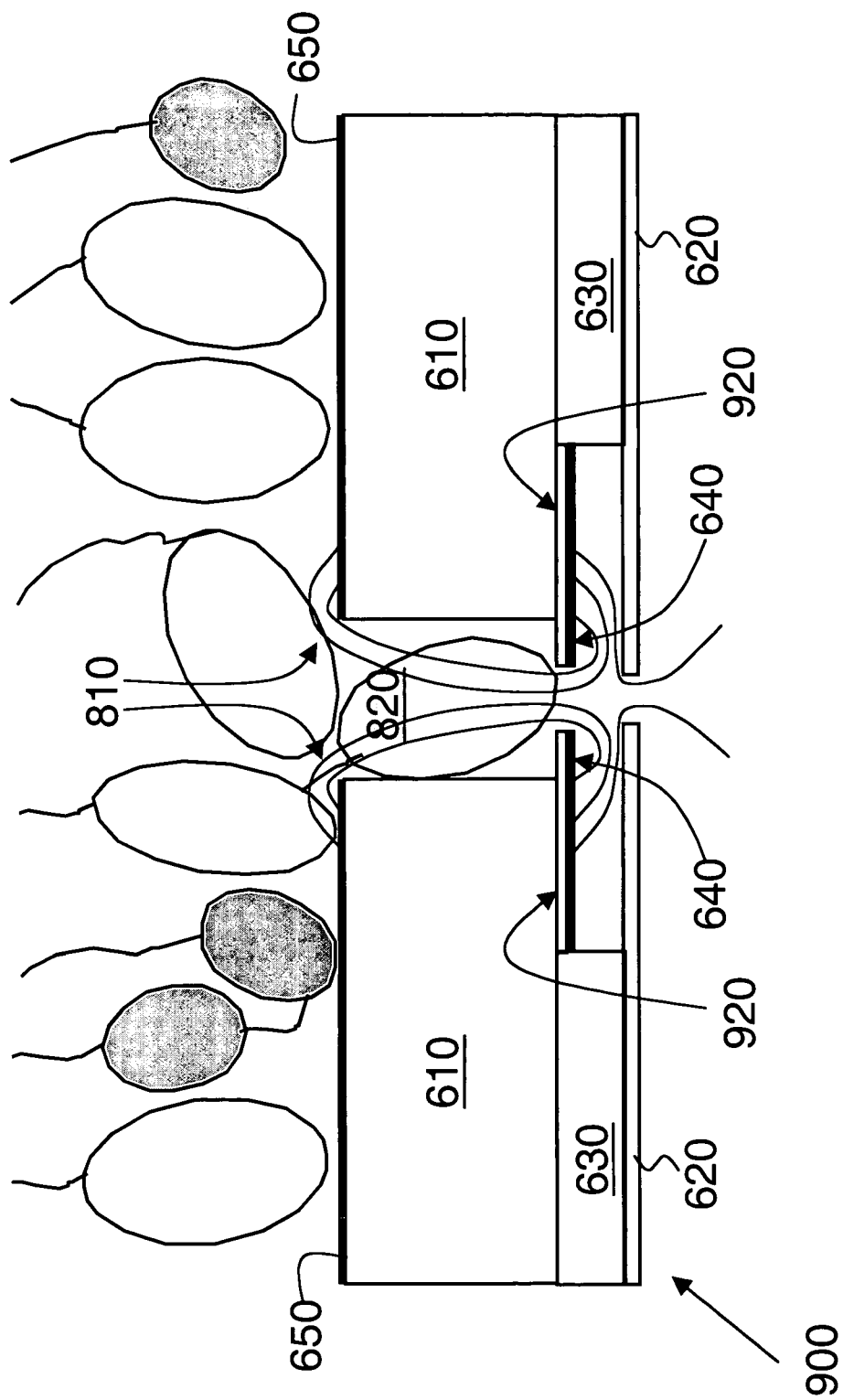
FIG. 9 shows an embodiment of the invention having an electrode and/or an insulator laterally extending into a channel.

FIG. 9 shows operation of an interface 900 which is a variation of interface 600. In interface 900, electrode 640 and/or an insulating intermediate layer 920 is/are extended partway into the channel passing through first layer 610. The example of FIG. 9 shows both electrode 640 and intermediate layer 920 extending into the channel. Such reduction of the minimum channel diameter reduces the electrical power required to excite cell 820, because the impedance of electrode 640 increases. A part of the cell 820 located close to the small opening in electrode 640 and intermediate layer 920 will be depolarized. Extension of electrode 640 in this manner also further increases its surface area, which desirably reduces the rate of electrochemical erosion of electrode 640.

Figure 10:
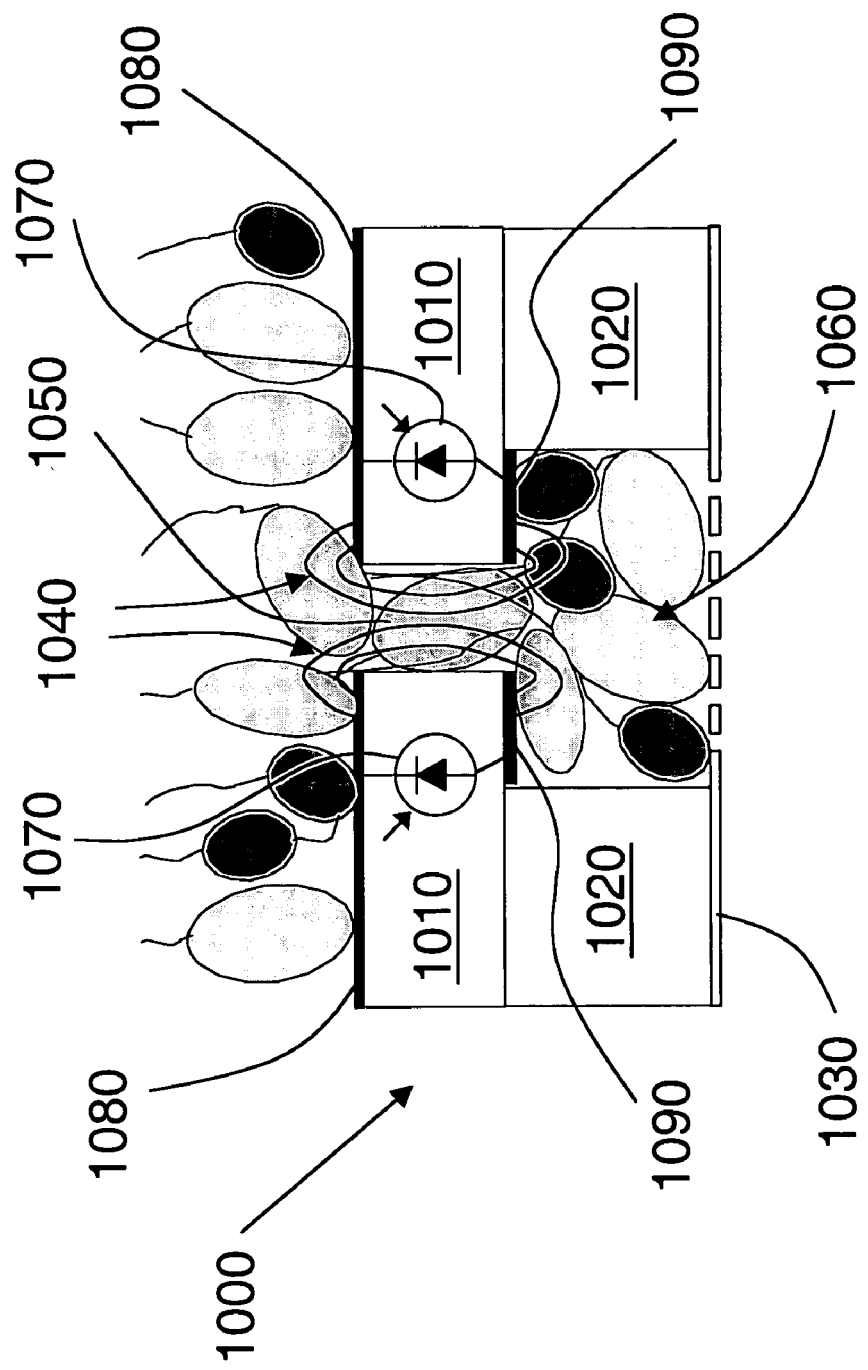
FIG. 10 shows an embodiment of the invention having photosensitive circuitry connected to the electrodes, and having a perforated stop layer at the bottom to prevent cell migration past the channel while allowing nutrient flow.

FIG. 10 shows operation of an interface 1000 according to another embodiment of the invention. In the embodiment of FIG. 10, a first layer 1010 and a second layer 1020 form a membrane analogous to membrane 110 of FIG. 1. A channel passes through both first layer 1010 and second layer 1020, where the channel diameter in second layer 1020 is larger than the channel diameter in first layer 1010. The thickness of layers 1010 and 1020 together is less than 0.5 mm. As shown on FIG. 10, the thickness of second layer 1020 is on the order of several times a typical cell dimension, to provide room for formation of a controlled retinal tuft within second layer 1020. Layer 1010 preferably has a thickness between about 5 microns and about 50 microns. Layer 1020 preferably has a thickness between about 5 microns and about 100 microns. A stop layer 1030 is disposed such that second layer 1020 is in between first layer 1010 and stop layer 1030.

The function of stop layer 1030 is to prevent uncontrolled growth of a retinal tuft past stop layer 1030, while permitting nutrients to flow to a cell (or cells) within the channel passing through layers 1010 and 1020. Stop layer 1030 is shown as having several small holes aligned to the channel through layer 1020. Preferably, these holes each have a diameter of less than about 5 microns, to prevent cell migration through the holes. Alternatively, stop layer 1030 could have a single small hole per channel, as shown on FIG. 6. More generally, stop layer 1030 can be either an impermeable membrane having at least one hole in it large enough to permit nutrient flow and small enough to prevent cells from moving through it, or a membrane which is permeable to nutrient flow.

An electrode 1090 is disposed on a surface of first layer 1010 facing second layer 1020, and another electrode 1080 is disposed on a surface of first layer 1010 facing away from second layer 1020. A photo-sensitive circuit 1070 (e.g., a photodiode, a phototransistor, etc.) is fabricated within first layer 1010 and is connected to electrodes 1080 and 1090. Electrode 1080 is preferably transparent to light and/or patterned in such a way that allows for light penetration to photo-sensitive circuit 1070.

The embodiment of FIG. 10 provides photo-sensitive circuit 1070 connected to electrodes 1080 and 1090. Accordingly, it is preferable for layer 1010 to be fabricated from a light-sensitive material permitting fabrication of photo-sensitive circuitry 1070 (e.g., any of various compound semiconductors such as GaAs and the like). Furthermore, for this embodiment, it is convenient for layers 1020 and 1030 to be materials compatible with the processing technology of the material of layer 1010. For example, layers 1020 and 1030 can be polymers (e.g., photoresists) or inorganic materials (e.g., oxides or nitrides). Channels through layers 1010 and 1020 (and holes through layer 1030) are preferably formed via lithography, in order to enable rapid fabrication of devices having a large number of channels. Since the materials indicated above are not typically bio-compatible, biological passivation of embodiments of the invention made with such materials is preferred. Suitable biological passivation techniques for such materials are known in the art.

In operation of interface 1000, light impinging on photo-sensitive circuit 1070 leads to generation of a potential difference between electrodes 1080 and 1090. Optionally, electronic amplification of the signal of photo-sensitive circuit 1070 is provided by amplification circuitry (not shown) to increase the signal at electrodes 1080 and 1090 responsive to illumination of photo-sensitive circuit 1070. The potential difference between electrodes 1080 and 1090 provides an electric field 1040 passing through a cell 1050 within the channel. Excitation of cell 1050 by electric field 1040 provides selective excitation of the retina, as shown on FIG. 5.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art.

For example, additional perforations can be included in the membrane to assist and/or ensure flow of nutrients. The diameter of such perforations should be smaller than the diameter of the channels to avoid neural cell migration through these additional perforations (i.e., tuft formation), but large enough to ensure a flow of nutrients. Specific growth factor(s) or surface coatings can be used to ensure migration of a particular cell group, e.g. only bipolar cells, or even a specific type of bipolar cell (e.g., "on" or "off" cells). Also, the interface can have some channels or perforations for stimulation purposes while other channels or perforations can be designed for mechanical anchoring to neural tissue The present invention is not limited to placement of the interface under the neural tissue since the interface can also be placed over or within the neural tissue. The interface can be used as a prosthetic device to connect to various kinds of neural tissue and is not limited to a retinal prosthesis or interface.

The interface has been discussed in light of electrically stimulating a select group of neural cells, however, the interface could also be used to measure signals generated in neural cells due to an external trigger/excitation, for example, signals generated in retinal cells due to light excitation.

In the discussion of FIG. 10, a preferred lithographic fabrication approach for the embodiment of FIG. 10 was discussed. Likewise, laser processing was discussed in connection with the embodiment of FIG. 6. The invention is not limited to any one fabrication method. Thus the use of lithography is not restricted to the embodiment of FIG. 10. Similarly, the use of laser processing is not restricted to the embodiment of FIG. 6.

All such variations are considered to be within the scope and spirit of the present invention as defined by the following claims and their legal equivalents.

What is claimed is:

1. An interface for selectively making electrical contact to a plurality of neural cells in a biological neural network, said interface comprising:

a) a membrane comprising a first and a second side having a thickness of less than 0.5 mm and including a plurality of channels passing through said thickness of said membrane, said membrane adapted to be disposed in proximity to said biological neural network, whereby said neural cells are capable of migrating into said channels; and b) a plurality of first electrodes disposed within said channels, wherein said channels including said electrodes are open;

wherein sufficient space is present in said channels to permit migration of at least one of said neural cells to pass from said first side of the membrane toward the other said second side of the membrane through said channels.

2. The interface of claim 1, wherein said membrane thickness is in a range from about 5 microns to about 100 microns.

3. The interface of claim 1, wherein said first electrodes are in physical contact with said neural cells.

4. The interface of claim 1, wherein said first electrodes are spaced apart from said neural cells.

5. The interface of claim 1, wherein said biological neural network comprises a brain cortex neural network.

6. The interface of claim 1, wherein said biological neural network comprises a retinal neural network.

7. The interface of claim 6, wherein said membrane is disposed subretinally.

8. The interface of claim 1, wherein said first electrodes are connected to a plurality of photo-sensitive circuits.

9. The interface of claim 1, wherein said first electrodes are coated with a high surface area layer, whereby electrochemical erosion of said electrodes is substantially reduced.

10. The interface of claim 1, further comprising i) a plurality of wires connected to said first electrodes and disposed on a surface of said membrane, and ii) an insulating layer disposed on said surface and covering said wires.

11. The interface of claim 1, further comprising a stop layer disposed on a surface of said membrane facing away from said biological neural network, whereby cellular migration past said stop layer is substantially prevented.

12. The interface of claim 11, wherein said stop layer comprises pores overlapping with said channels, said pores being smaller than said channels.

13. The interface of claim 11, wherein said stop layer is permeable to nutrient flow.

14. The interface of claim 1, wherein said plurality of channels is arranged in a two-dimensional array.

15. The interface of claim 1, wherein each of said channels is substantially circular.

16. The interface of claim 15, wherein each of said channels has substantially uniform diameter along its length, and wherein said diameter is in a range from about 5 microns to about 50 microns.

17. The interface of claim 15, wherein said membrane comprises a first layer facing said biological neural network, and a second layer facing away from said biological neural network, and wherein each of said channels has a larger diameter in said second layer than in said first layer.

18. The interface of claim 17, wherein said first electrodes are disposed on a surface of said first layer facing said second layer.

19. The interface of claim 17, wherein said first layer comprises a semiconductor layer.

20. The interface of claim 17, wherein said first layer comprises a plurality of photo-sensitive circuits connected to said electrodes.

21. The interface of claim 17, further comprising a second electrode disposed on a surface of said first layer facing said biological neural network.

22. The interface of claim 21, wherein said second electrode is common to all of said plurality of channels.

23. The interface of claim 21, wherein said second electrode is transparent.

24. The interface of claim 17, further comprising a stop layer affixed to a surface of said second layer facing away from said first layer, whereby cellular migration past said stop layer is substantially prevented.

25. The interface of claim 24, wherein said stop layer comprises pores overlapping with said channels, said pores being smaller than said channels.

26. The interface of claim 24, wherein said stop layer is permeable to nutrient flow.

27. The interface of claim 17, further comprising an intermediate layer disposed in between said first and second layers, wherein said channels have a smaller diameter within said intermediate layer than within said first layer.

28. The interface of claim 27, wherein said electrode is disposed on a surface of said intermediate layer facing said second layer.

29. A method for selectively making electrical contact to a plurality of neural cells in a biological neural network, said method comprising:

a) positioning a membrane in proximity to said biological neural network, said membrane having a first and a second side, a thickness of less than 0.5 mm and including a plurality of channels passing through said thickness of said membrane, whereby said neural cells are capable of migrating into said channels; and b) providing a plurality of electrodes disposed within said channels, wherein said channels including said electrodes are open;

wherein sufficient space is present in said channels to permit migration of a least one of said neural cells to pass from said first side of the membrane toward the other said second side of the membrane through said channels.

30. The method of claim 29, further comprising allowing at least one of said neural cells to migrate into at least one of said channels.

31. The method of claim 29, further comprising inducing at least one of said neural cells to migrate into at least one of said channels.

* * * * *